(12) United States Patent
Wolfson

(10) Patent No.: US 11,723,554 B2
(45) Date of Patent: Aug. 15, 2023

(54) ADJUSTABLE TIBIAL SIZER

(71) Applicant: DEPUY IRELAND UNLIMITED COMPANY, County Cork (IE)

(72) Inventor: David Wolfson, West Yorkshire (GB)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 173 days.

(21) Appl. No.: 17/123,784

(22) Filed: Dec. 16, 2020

(65) Prior Publication Data
US 2021/0186375 A1    Jun. 24, 2021

(51) Int. Cl.
*A61B 5/107* (2006.01)
*A61B 17/15* (2006.01)
*A61B 5/00* (2006.01)

(52) U.S. Cl.
CPC .......... *A61B 5/1072* (2013.01); *A61B 5/4585* (2013.01); *A61B 5/6878* (2013.01); *A61B 17/157* (2013.01)

(58) Field of Classification Search
CPC combination set(s) only.
See application file for complete search history.

(56) References Cited

U.S. PATENT DOCUMENTS

2017/0049527 A1* 2/2017 Matsuda .............. A61B 5/4528
2019/0336141 A1   11/2019 Erickson et al.

FOREIGN PATENT DOCUMENTS

CN         209951262 U    1/2020

OTHER PUBLICATIONS

SIGMA High Performance Partial Knee Unicondylar Surgical Technique, 140082-200512 DSUS/EMEA, DSUS/JRC/1114/0582 Rev. 3, 2017, 2019, 2020, 28 Pages.
GB Search Report From Corresponding GB Patent Application GB1919043.8 dated Jun. 23, 2020, 3 Pages.

* cited by examiner

*Primary Examiner* — Sameh R Boles

(57) ABSTRACT

This disclosure relates to an adjustable tibial sizer for use in knee arthroplasty, the sizer includes a two-part body comprising: a first body portion, a second body portion, and a connection element extending therebetween. Each of the first and second body portions includes a ramp surface configured for simultaneous movement of the first body portion relative to the second body portion in an anterior-posterior direction and a medial-lateral direction, and method of use thereof.

11 Claims, 6 Drawing Sheets

ADJUSTABLE TIBIAL SIZER

This application claims priority to GB1919043.8, which was filed on Dec. 20, 2019 and is expressly incorporated herein by reference.

TECHNICAL FIELD

The disclosure relates to an adjustable tibial sizer for determining the appropriate size of a tibial base plate in unicompartmental knee replacement surgery, and methods of use thereof.

BACKGROUND

Joint arthroplasty is a well-known surgical procedure by which a diseased and/or damaged joint is replaced by a prosthetic component. A typical knee prosthesis includes a tibial tray, a femoral component, and a polymer insert or bearing positioned between the tibial tray and the femoral component. In unicompartmental knee replacement surgery, also referred to as "partial" knee replacement surgery, only a portion of the knee is replaced with metal and plastic. This procedure is an alternative to a "total" knee replacement for patients where the damaged bone or cartilage is limited to the medial or lateral compartments of the knee.

During knee arthroplasty surgery, a tibial sizer or set of sizers, may be used to estimate the appropriate size tibial base plate, with respect to both the anterior/posterior direction and the medial/lateral direction.

Tibial size selection for unicompartmental knee replacement is normally undertaken by introducing sized templates to the resected bone. These are then assessed for both anterior/posterior fit, medial/lateral fit, and thickness. The surgical instrument tray necessarily includes a large number of different sized templates. This has cost implications, and also adds to the weight of the instrument tray. Furthermore, during surgery the surgeon must swap different sized templates in order to try out different sizes. This requires the surgeon to keep track of which size of template(s) has already been tried, and also prolongs the surgical time whilst the scrub nurse locates the requested next size of template.

SUMMARY

According to a first aspect, there is provided an adjustable tibial sizer for use in knee arthroplasty, the sizer includes a two-part body comprising:
  a first body portion
  a second body portion, and
  a connection element extending therebetween,
  wherein each of the first and second body portions includes a ramp surface configured for simultaneous movement of the first body portion relative to the second body portion in an anterior-posterior and a medial-lateral direction.

In some constructions, the first portion includes a posterior end and an anterior end and a longitudinal axis extending therebetween, and wherein the ramp surface of each of the first and second body portions is set an angle relative to the longitudinal axis.

In some constructions, an anterior-posterior dimension of the sizer is defined between a most anteriorly placed point on the first body portion and a most posteriorly placed point on the second body portion, and a medial-lateral dimension of the sizer is defined between a most medially placed point on the first body portion and a most laterally placed point on the second body portion, and wherein the angle of the ramp surface of the second body portion relative to the longitudinal axis provides a pre-determined ratio of the anterior-posterior dimension to the medial-lateral dimension.

The ramp surfaces provided on the first and second body portions may be in sliding contact. For example, one of the ramp surfaces on the first or second body portions may include a channel or groove, and the ramp surface on the other of the first and second body portions may include a rail configured for slidable receipt within the channel. In some constructions, the ramp surface is provided on a platform. The platform may be located on a surface of the body that is positioned superior, when in use.

In some constructions, the first portion includes a first generally flat inner peripheral surface and the second body portion includes a second generally flat inner peripheral surface, wherein
  when the tibial sizer is in a first configuration having a first anterior-posterior dimension and a first medial-lateral dimension, the first inner peripheral surface of the first body portion is parallel with the second inner peripheral surface of the second body portion, and wherein
  when the tibial sizer is in a second configuration having a second anterior-posterior dimension and a second medial-lateral dimension, the first inner peripheral surface of the first body portion is parallel with the second inner peripheral surface of the second body portion.

The adjustable tibial sizer may include a head defined by the first body portion and the second body portions, and a handle extending from the first body portion.

The head of the adjustable tibial sizer may include anterior, posterior, lateral and medial outer peripheral surfaces. One of the lateral or medial outer peripheral surfaces may be curved and the other one of the lateral or medial outer peripheral surface may be generally flat.

The head of the adjustable tibial sizer may include anterior, posterior, lateral and medial outer peripheral surfaces shaped to generally correspond to posterior, lateral and medial outer peripheral surfaces, respectively, of a tibial base plate of a unicompartmental knee prosthesis.

The handle of the adjustable tibial sizer may include a channel extending along the handle in a longitudinal direction. A first end of the connection element may be configured to be slidably positioned within the channel, and a second end of the connection element may be secured to the second body portion. The connection element may be a hinge.

The adjustable tibial sizer may also indicia for indicating a suggested size of tibial base plate based on the ratio of the anterior-posterior dimension to the medial-lateral dimension of the base plate.

According to a second aspect, there is provided a method of using an adjustable tibial sizer to aid in selecting an appropriately sized tibial base plate, the method comprising the steps of:
  using an adjustable tibial sizer comprises a two-part body which comprises a first body portion, a second body portion, and a connection element extending therebetween, wherein each of the first and second body portions includes a ramp surface configured for simultaneous movement of the first body portion relative to the second body portion in an anterior-posterior direction and a medial-lateral direction;

placing the adjustable tibial sizer on a cut surface of a resected tibia so that a most medially located surface of the first body portion is against a surface created by a sagittal cut, and a most anteriorly placed point on the first body portion corresponds with a most anteriorly placed point on the tibia;

moving the second body portion relative to the first body portion, simultaneously in the anterior-posterior direction and the medial-lateral direction until a most posteriorly placed point on the second body portion corresponds with a most posteriorly placed point on the tibia; and measuring the ratio of an anterior-posterior dimension of the adjustable tibial sizer to a medial-lateral dimension of the adjustable tibial sizer.

The method may also include the step of selecting an appropriately sized tibial base plate having a ratio of an anterior-posterior dimension to a medial-lateral dimension that generally corresponds with the measured ratio of the anterior-posterior dimension to the medial-lateral dimension of the adjustable tibial sizer.

BRIEF DESCRIPTION OF THE DRAWINGS

The detailed description particularly refers to the following figures, in which.

DETAILED DESCRIPTION OF THE DRAWINGS

Figure 1:
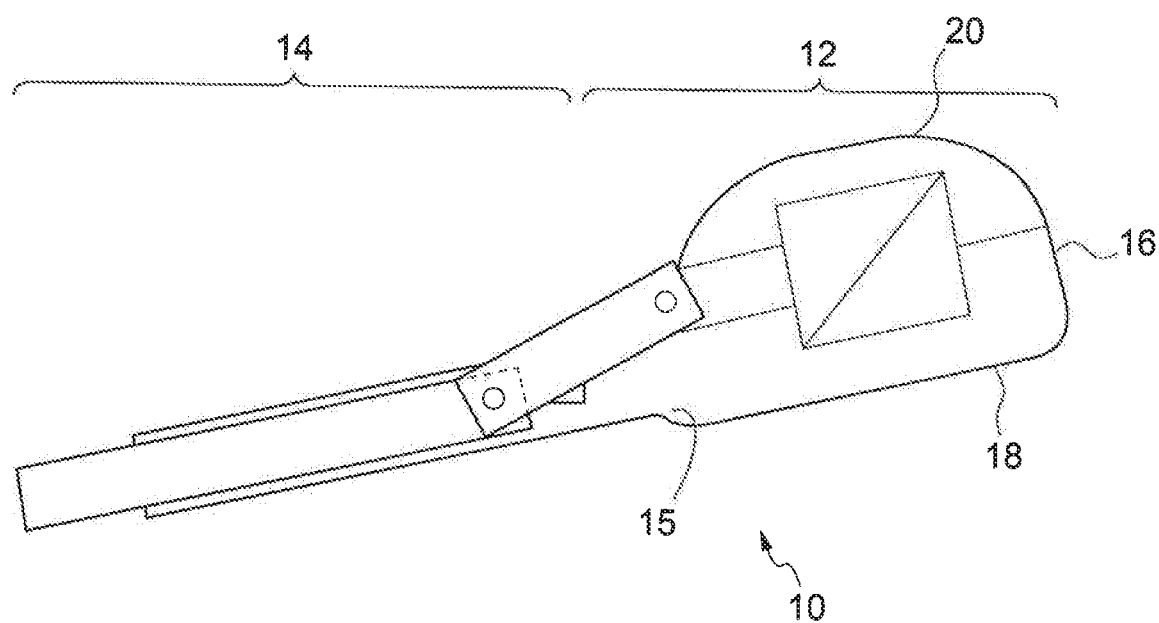
FIGS. 1, 3, and 6 are schematic views of an exemplary construction of the adjustable tibial sizer in a first, initial, configuration.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure as defined by the appended claims.

Referring now to FIGS. 1-6, an exemplary construction of the adjustable tibial sizer 10 for use in sizing and selecting a tibial base plate is shown. An exemplary tibial base plate (identified as a metal-back tray) is shown and described in the SIGMA® High Performance Partial Knee Unicondylar Surgical Technique (2020), which is expressly incorporated herein by reference. It should be appreciated that such tibial base plates may come in various sizes, including differences in their anterior-posterior and medial-lateral dimensions. As shown in FIG. 1, the sizer 10 includes a handle 14 and a head 12, which is adjustable to provide a surgeon with approximations of the anterior-posterior and medial-lateral dimensions of tibial base plates of various sizes and thereby assist the surgeon in the selection of a tibial base plate sized appropriately for a particular patient's anatomy.

The head 12 includes an anterior outer peripheral surface 15, a posterior outer peripheral surface 16, a medial outer peripheral surface 18, and a lateral outer peripheral surface 20. The medial outer peripheral surface 18 is generally flat and the lateral outer peripheral surface 20 is curved. The head also includes an inferiorly placed bone-contacting surface (not shown), which is configured to rest on the surface of a resected tibial plateau when in the sizer is in use.

In some constructions of the adjustable sizer, the anterior, posterior, medial and lateral outer peripheral surfaces 15, 16, 18, 20, respectively are shaped to generally correspond to the posterior, medial, and lateral outer peripheral surfaces, respectively, of the tibial base plate or tray of a unicondylar or unicompartmental knee prosthesis.

Figure 2:
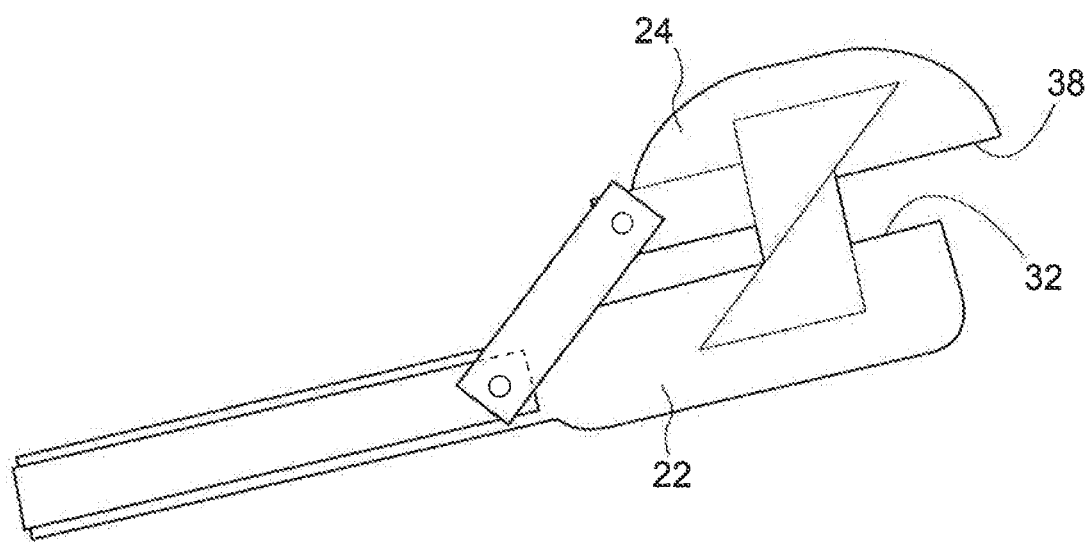
FIGS. 2, 4, and 5 are schematic views of the exemplary construction of the adjustable tibial sizer in a second, expanded, configuration.
Figure 3:
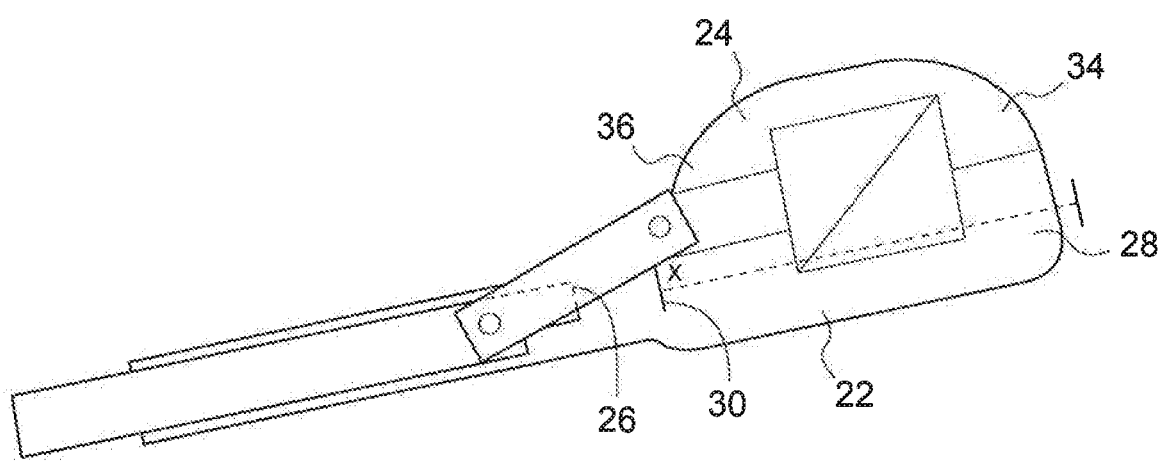

Referring now to FIG. 3, the head includes a two-part body that includes a first body portion 22 and a second body portion 24 that are connected to each other via a connection element, here shown in the form of a jointed arm 26. As shown, the body portions 22, 24 are configured to move between an initial position (see FIGS. 1 and 3) and a number of expanded configurations, one of which is shown in FIGS. 2 and 4).

The first body portion 22 includes a posterior end 28 and an anterior end 30. A longitudinal axis X extends between the posterior end 28 and the anterior end 30. The first body portion 22 includes a generally flat inner peripheral surface 32.

The second body portion 24 includes a posterior end 34 and an anterior end 36. The second body portion 24 includes a generally flat inner peripheral surface 38. It should be appreciated that one or both of the posterior ends of the body portions 22, 24 may include inferior-superior walls configured to hook over the posterior tibial cortex to facilitate positioning of the sizer.

Figure 4:
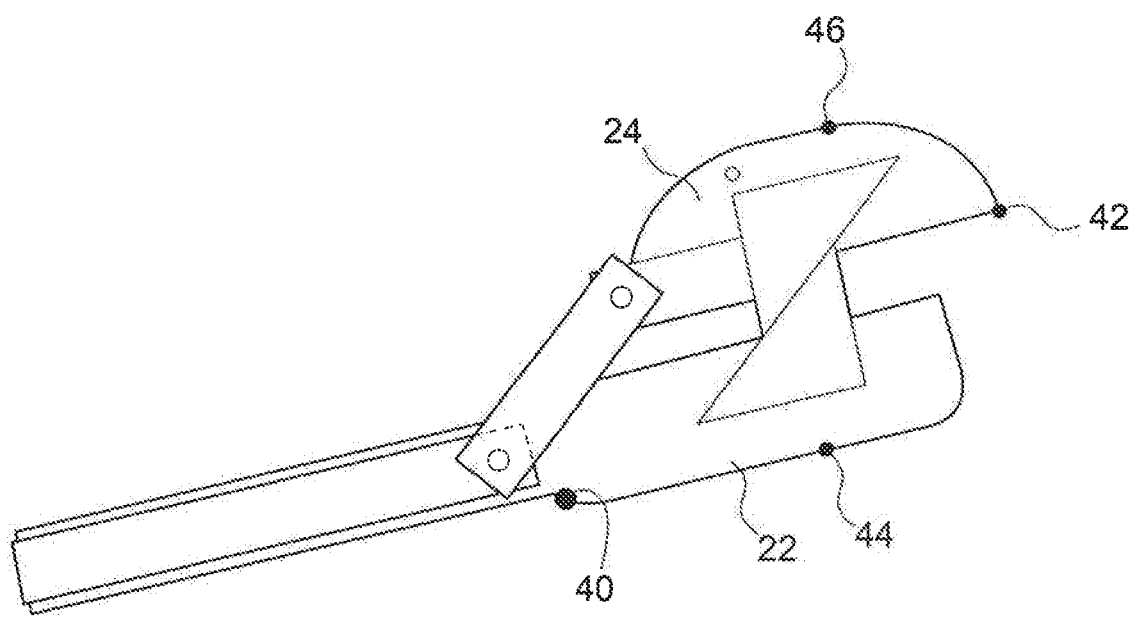
Figure 5:
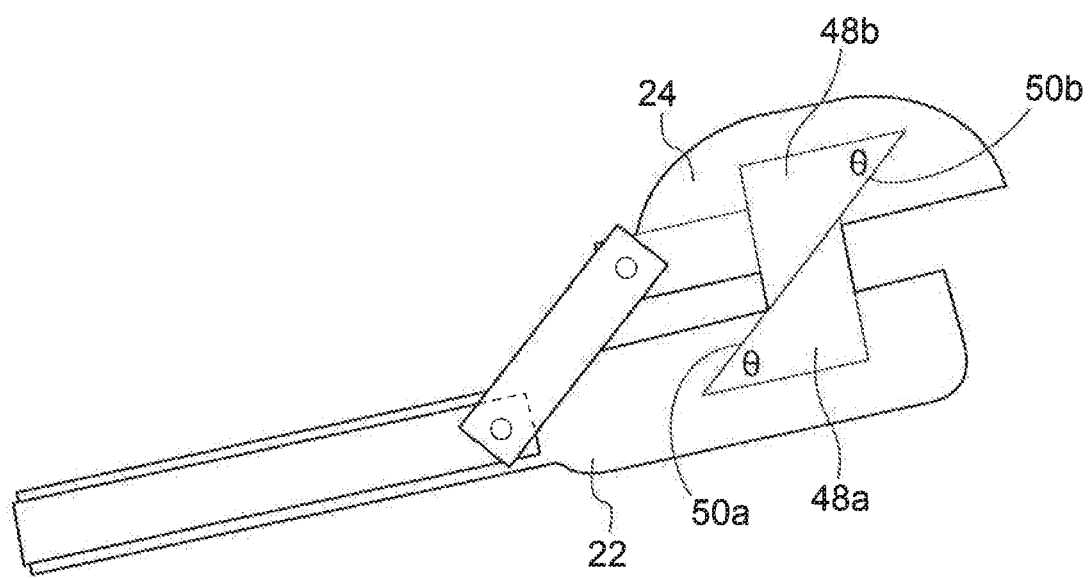

As shown in, for example, FIG. 4, an anterior-posterior dimension ($Dim_{A-P}$) of the sizer is defined between a most anteriorly placed point 40 on the first body portion 22 and a most posteriorly placed point 42 on the second body portion 24. A medial-lateral dimension ($Dim_{M-L}$ of the sizer is defined between a most medially placed point 44 on the first body portion 22, and a most laterally placed point 46 on the second body portion 24. It should be appreciated that the anterior-posterior dimensions ($Dim_{A-P}$) and medial-lateral dimensions ($Dim_{M-L}$) change depending on the position of the body portions 22, 24, with the dimensions being smaller when the body portions 22, 24 are in the initial position (see FIGS. 1 and 3) and larger when the body portions are in one of the expanded positions (see, for example, FIGS. 2 and 4).

A superiorly placed surface of each of the first and second body portions 22,24 includes a platform 48a, 48b on which a ramp surface 50a, 50b is provided. Each ramp surface 50a, 50b is configured to facilitate simultaneous movement of the first body portion 22 relative to the second body 24 portion in the anterior-posterior direction and the medial-lateral direction.

In the construction shown, each platform has a generally triangular shape. The platform 48a of the first body portion 22, includes a ramp surface 50a. The platform 48b of the second body portion 24, includes a ramp surface 50b.

To facilitate simultaneous movement of the first body portion relative to the second body portion in the anterior-posterior and medial-lateral directions, the ramp surfaces are configured such that they are in sliding contact. Such contact may be achieved by the provision of a male member on one of the ramp surfaces, and a female member on the other one of the ramp surfaces. For example, one of the ramp surfaces may include a channel or groove extending along its length, and the other one of the ramp surfaces may include a rail or lip configured for slidable receipt within the channel or groove.

The angle θ of each of the first and second ramp surfaces can be varied relative to the longitudinal axis X in order to provide a pre-determined ratio of the anterior-posterior dimension to the medial-lateral dimension of the adjustable tibial sizer. In the construction shown, the angle θ of each of the first and second ramp surfaces 50a, 50b relative to the longitudinal axis X is about 45°. In some constructions, the angle θ of the ramp surface of each of the first and second ramp surfaces can be varied relative to the longitudinal axis X so that the ratio of the anterior-posterior dimension to the medial-lateral dimension of the adjustable sizer remains constant as the first and second body portions are moved relative to each other. The ratio is defined to be consistent with the AP-ML ratio of the corresponding family of tibial base plates.

Figure 6:
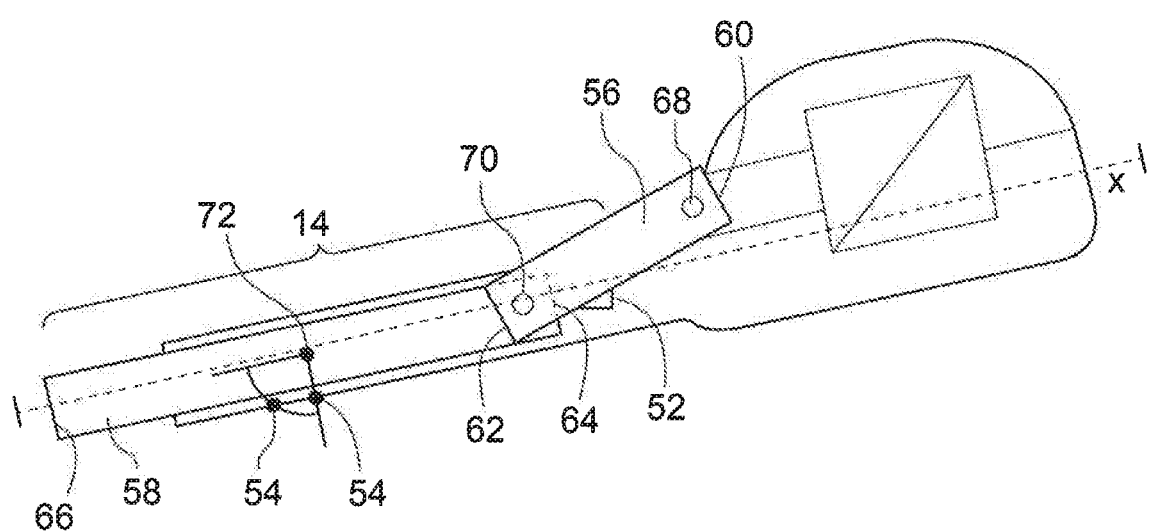

Turning now to FIG. 6 which shows the handle 14 of the adjustable tibial sizer in greater detail. The handle extends in an anterior direction from an anterior region of the first body portion 22. The handle has a longitudinal axis that is contiguous with the longitudinal axis X of the first body portion in this embodiment. A slot 52 extends along at least a part of the length of the handle.

A first set of indicia 54 may be provided on the handle to provide an indication of an appropriate size of tibial base plate to be implanted during knee arthroplasty. For example, "size 1", "size 2," etc.

As noted above, the first and second body portions 22, 24 are movably connected via a connection element, shown here in the form of a jointed arm 26. The jointed arm includes a first arm portion 56 and a second arm portion 58.

The first arm portion 56 includes a posterior end 60 and an anterior end 62.

The second arm portion 58 includes a posterior end 64 and an anterior end 66. The posterior end 60 of the first arm portion 56 is attached to a most anteriorly placed point (not shown) on the second body portion 24 via a pivot, such as a pin 68.

The anterior end 62 of the first arm portion 56 is attached to the posterior end 64 of the second arm portion 58 via a pivot, such as a pin 70. Pin 70 is of sufficient length that it protrudes from an inferior surface (not shown) of the second arm portion 58 and is configured to be slidably received within the slot 52 of the handle.

The pin 70 guides the sliding movement of the second arm portion 58 in an anterior-posterior direction along the handle, which in turn facilitates the movement of the second body portion 24 simultaneously in the anterior-posterior and medial-lateral directions due to the linkage via the first arm portion 56.

One or more reference markings, such as, for example, marking 72 may be provided on the second arm portion. The position of this reference marking in respect of the indicia 54 on the handle will inform the surgeon of the appropriately sized tibial base plate.

In other embodiments, the sizer may include a dial rotatable between discrete positions. When rotated, the dial is configured to engage the second arm portion 58 to move it along the handle and thereby move the body portions 22, 24 to discrete positions corresponding to different sizes of tibial base plates. The dial may include a marking at each position showing a corresponding size of tibial base plate. It should be appreciated that the dial may take the form of a wheel, knob, barrel, or other rotatable component. In still other embodiments, the sizer may include a lever movable between discrete positions to slide the second arm portion 58 to different positions corresponding to different sizes of tibial base plates.

The adjustable tibial sizer shown in FIGS. 1 and 2 may be used to determine the appropriate size of tibial base plate to be implanted on (i) a resected lateral compartment of the right knee using an anterior surgical approach, (ii) a resected medial compartment of the right knee using an posterior surgical approach, (iii) a resected medial compartment of the left knee using an anterior surgical approach, and (iv) a resected lateral compartment of the left knee using an posterior surgical approach. The surgeon is using a different surgical approach, it is envisaged that the device could be flipped over or inverted, or alternatively, a mirror image of the device may be provided.

To undertake sizing, the bone-contacting surface (not shown) of the head portion 12 of the sizer is placed onto the tibial plateau, with the generally flat medial peripheral edge 18 of the first body portion 22 resting against a surface of a sagittal cut, and the most anteriorly placed point 40 on the first body portion 22 overlying the most anteriorly placed point (not shown) on the tibial plateau.

In this first, initial, configuration, (shown in FIGS. 1 and 3) the adjustable tibial sizer has a first anterior-posterior dimension ($Dim_{A1-P1}$) and a first medial-lateral dimension ($Dim_{M1-L1}$). The first inner peripheral surface 34 of the first body portion 22 is parallel with the second inner peripheral surface 38 of the second body portion 24.

With the first body portion 22 remaining in a stationary position on the tibial plateau, the surgeon can grip the handle 12 and use his thumb to slide the anterior end 66 of the second arm portion 58 of the jointed arm 26 posteriorly within slot 52. This movement causes the second body portion 24 to move simultaneously in a posterior-lateral direction relative to the stationary first body portion 22. During this movement, the ramp surface 50b on the second body portion 24 will slide along the ramp surface 50a of the stationary first body portion 22.

The surgeon continues to slide the anterior end 66 of the second arm portion 58 of the jointed arm 26 posteriorly within slot 52 until the second body portion has been moved sufficiently in the anterior-posterior direction (whilst being simultaneously moved in the medial-lateral direction) such that the most posteriorly placed point 42 on the second body portion 24 overlies the most posteriorly placed point (not shown) on the tibial plateau.

In this second, expanded, configuration (shown in FIGS. 2 and 4), the adjustable tibial sizer has a second anterior-posterior dimension ($Dim_{A2-P2}$), which is greater than the first anterior-posterior dimension ($Dim_{A1-P1}$), and a second medial-lateral dimension ($Dim_{M2-L2}$), which is greater than the first medial-lateral dimension ($Dim_{M1-L1}$).

During movement of the tibial sizer from the first, initial, configuration, into the second, expanded, configuration the first inner peripheral surface 32 of the first body portion 22 remains parallel with the second inner peripheral surface 38 of the second body portion 24.

Due to the construction of the adjustable sizer, and the in-built simultaneous movement of the second body portion relative to the first body portion in the anterior-posterior and medial-lateral direction, the sizer will provide a surgeon with an approximation of both the anterior-posterior and medial-lateral dimensions.

The surgeon can then view the position of the reference marking 72 in respect of the indicia 54 on the handle in order to select an appropriately sized tibial base plate.

It should be appreciated that in other embodiments the adjustable head may take other configurations to assist the surgeon in sizing and selecting a tibial base plate. For example, the body portions 22, 24 may be connected via a pin in track arrangement in which the track is configured to guide the movement of the pin along a predefined path. As the pin is moved along the track, the body portions 22, 24 are moved to different relative positions, thereby increasing or decreasing the medial-lateral and anterior-posterior dimensions of the adjustable head. In another embodiment, the body portions 22, 24 may be connected via a cam and pin arrangement, with the cam shaped and sized to move the pin to different positions. As the cam is rotated on one body portion, the pin on other body is configured to slide along the cam to change the relative positions of the body portions, thereby increasing or decreasing the medial-lateral and anterior-posterior dimensions of the adjustable head to correspond to different tibial base plate sizes. In still other embodiments, the sliding contact between the body portions may be replaced with link arms in an alternative 4-bar linkage configuration.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present disclosure and fall within the spirit and scope of the present disclosure as defined by the appended claims.

The invention claimed is:

1. An adjustable tibial sizer for use in knee arthroplasty, the sizer comprising:
   a two-part body comprising:
      a first body portion
      a second body portion, and
      a link arm extending therebetween,
   wherein each of the first and second body portions includes a ramp surface configured for simultaneous movement of the first body portion relative to the second body portion in an anterior-posterior direction and a medial-lateral direction.

2. The adjustable tibial sizer of claim 1, wherein the first portion includes a posterior end and an anterior end and a longitudinal axis extending therebetween, and wherein the ramp surface of each of the first and second body portions is set an angle relative to the longitudinal axis.

3. The adjustable tibial sizer of claim 2, wherein
   an anterior-posterior dimension of the sizer is defined between a most anteriorly placed point on the first body portion and a most posteriorly placed point on the second body portion,
   a medial-lateral dimension of the sizer is defined between a most medially placed point on the first body portion and a most laterally placed point on the second body portion, and
   the angle of the ramp surface of the second body portion relative to the longitudinal axis provides a pre-determined ratio of the anterior-posterior dimension to the medial-lateral dimension.

4. The adjustable tibial sizer of claim 3, wherein:
   the first body portion includes a first generally flat inner peripheral surface and the second body portion includes a second generally flat inner peripheral surface, and
   when the tibial sizer is in a first configuration having a first anterior-posterior dimension and a first medial-lateral dimension, the first inner peripheral surface of the first body portion is parallel with the second inner peripheral surface of the second body portion, and when the tibial sizer is in a second configuration having a second anterior-posterior dimension and a second medial-lateral dimension, the first inner peripheral surface of the first body portion is parallel with the second inner peripheral surface of the second body portion.

5. The adjustable tibial sizer of any of claim 1, wherein the ramp surfaces are in sliding contact.

6. The adjustable tibial sizer of claim 5, wherein one of the ramp surfaces on the first or second body portions includes a channel, and wherein the ramp surface on the other of the first and second body portions comprises a rail configured for slidable receipt within the channel.

7. The adjustable tibial sizer of claim 1, wherein the sizer comprises:
   a head including first body portion and the second body portion, and
   a handle extending from the first body portion.

8. The adjustable tibial sizer of claim 7, wherein the head includes anterior, posterior, lateral and medial outer peripheral surfaces, and wherein one of the lateral or the medial outer peripheral surfaces is curved and the other one of the lateral or the medial outer peripheral surfaces is generally flat.

9. The adjustable tibial sizer of claim 7, wherein the head includes anterior, posterior, lateral and medial outer peripheral surfaces shaped to generally correspond to posterior, lateral and medial outer peripheral surfaces, respectively, of a tibial base plate of a unicompartmental knee prosthesis.

10. The adjustable tibial sizer of any of claim 7, wherein a channel extends along the handle in a longitudinal direction, wherein a first end of the connection element is configured to be slidably positioned within the channel, and a second end of the connection element is secured to the second body portion.

11. The adjustable tibial sizer of any of claim 1, comprising indicia for indicating a suggested size of tibial base plate based on the ratio of the anterior-posterior dimension to the medial-lateral dimension of the base plate.

* * * * *